(12) United States Patent
Anderson (10) Patent No.: US 10,034,677 B2
(45) Date of Patent: Jul. 31, 2018

(54) CUSTOMIZABLE JOINT REPLACEMENT APPARATUS

(71) Applicant: Greatbatch Ltd., Clarence, NY (US)

(72) Inventor: Daniel L. Anderson, Winona Lake, IN (US)

(73) Assignee: Greatbatch Ltd., Clarence, NY (US)

( * ) Notice: Subject to any disclaimer, the term of this patent is extended or adjusted under 35 U.S.C. 154(b) by 725 days.

(21) Appl. No.: 14/332,481

(22) Filed: Jul. 16, 2014

(65) Prior Publication Data

US 2015/0032113 A1    Jan. 29, 2015

Related U.S. Application Data

(60) Provisional application No. 61/857,366, filed on Jul. 23, 2013.

(51) Int. Cl.
| | | |
|---|---|---|
| A61B 17/58 | (2006.01) | |
| A61B 17/60 | (2006.01) | |
| A61F 2/00 | (2006.01) | |
| A61B 17/17 | (2006.01) | |
| A61B 17/15 | (2006.01) | |
| A61B 17/88 | (2006.01) | |
| A61B 17/56 | (2006.01) | |

(52) U.S. Cl.
CPC .......... *A61B 17/1764* (2013.01); *A61B 17/15* (2013.01); *A61B 17/155* (2013.01); *A61B 17/8863* (2013.01); *A61B 2017/568* (2013.01)

(58) Field of Classification Search
CPC ..... A61B 17/15; A61B 17/154; A61B 17/155; A61B 17/157; A61B 17/158; A61B 17/1764; A61B 17/1767; A61B 17/8863
See application file for complete search history.

(56) References Cited

U.S. PATENT DOCUMENTS

| | | | |
|---|---|---|---|
| 4,733,407 A | 3/1988 | Pathuis et al. | |
| 4,736,737 A | 4/1988 | Fargie et al. | |
| 7,824,181 B2 | 11/2010 | Sers | |
| 2004/0102866 A1 | 5/2004 | Harris et al. | |
| 2004/0260301 A1* | 12/2004 | Lionberger | A61B 17/155 606/88 |
| 2005/0148843 A1 | 7/2005 | Roose | |
| 2007/0288030 A1 | 12/2007 | Metzger et al. | |
| 2008/0161815 A1 | 7/2008 | Schoenefeld et al. | |
| 2008/0243191 A1* | 10/2008 | Tipirneni | A61B 17/742 606/280 |
| 2009/0087276 A1 | 4/2009 | Rose | |
| 2009/0088674 A1 | 4/2009 | Caillouette et al. | |

(Continued)

FOREIGN PATENT DOCUMENTS

EP    1669033 A1    6/2006

OTHER PUBLICATIONS

"EP Search", 14177772.2, dated Oct. 8, 2014.

*Primary Examiner* — Si Ming Ku
(74) *Attorney, Agent, or Firm* — Michael P. Horvath (57) ABSTRACT

In various examples, an apparatus includes an instrument body including a protrusion configured to be sized according to an anatomy of a bone of a patient. A guide is configured to guide an aspect of a resection procedure of the bone, wherein the protrusion, when sized, is configured to abut the patient's bone to maintain the instrument body in a first position with respect to the bone during at least part of the resection procedure.

20 Claims, 5 Drawing Sheets

(56) References Cited

U.S. PATENT DOCUMENTS

| | | | |
|---|---|---|---|
| 2009/0099567 A1* | 4/2009 | Zajac | A61B 17/155 |
| | | | 606/79 |
| 2009/0106984 A1* | 4/2009 | Braswell | B26B 13/22 |
| | | | 30/254 |
| 2010/0023015 A1 | 1/2010 | Park | |
| 2010/0191244 A1 | 7/2010 | White et al. | |
| 2014/0276854 A1* | 9/2014 | Schoenefeld | A61B 17/155 |
| | | | 606/87 |

* cited by examiner

CUSTOMIZABLE JOINT REPLACEMENT APPARATUS

CROSS REFERENCE TO RELATED APPLICATIONS

This application claims the benefit of priority to U.S. Provisional Application Ser. No. 61/857,366, filed on Jul. 23, 2013, entitled "CUSTOMIZABLE JOINT REPLACEMENT APPARATUS," which is incorporated by reference herein in its entirety.

BACKGROUND

The present invention relates to joint replacement procedures, and more specifically relates to a customizable apparatus for use during a joint replacement procedure.

Patient specific instruments for joint replacement procedures have been touted as being advantageous over "one-size-fits-all" instruments, such as, for instance, offering a faster process with fewer complications and faster recovery with less discomfort and a more natural feel than a joint replacement procedure performed with "one-size-fits-all" instruments. Some question whether a joint replacement procedure using patient specific instruments actually offers such advantages over a joint replacement procedure using "one-size-fits-all" instruments.

A joint replacement procedure using patient specific instruments typically requires several steps prior to the actual joint replacement procedure. For instance, magnetic resonance imaging of the joint is performed. Using the resulting images, a virtual implant is "virtually placed" on the knee to determine bone resection/instrument placement. Once that is complete, the patient specific instrument is designed, manufactured, and then delivered for the procedure. By using patient specific instruments, these extra steps can significantly delay and increase the costs of a joint replacement procedure in order to obtain the patient specific instruments. Such delays and increases in cost lead some to question whether the added time and expense is worth the purported benefits.

Overview

This overview is intended to provide an overview of subject matter of the present patent application. It is not intended to provide an exclusive or exhaustive explanation of the invention. The detailed description is included to provide further information about the present patent application.

The present inventors have recognized, among other things, that the present subject matter can be used to customize a joint replacement instrument apparatus according to the specific anatomy of a patient in a timely and cost-efficient manner. To better illustrate the apparatuses, systems, and methods described herein, a non-limiting list of examples is provided here:

Example 1 can include subject matter that can include an apparatus. An instrument body includes a protrusion configured to be sized according to an anatomy of a bone of a patient. A guide is configured to guide an aspect of a resection procedure of the bone, wherein the protrusion, when sized, is configured to abut the patient's bone to maintain the instrument body in a first position with respect to the bone during at least the aspect of the resection procedure.

In Example 2, the subject matter of Example 1 is optionally configured such that the instrument body includes more than one protrusion.

In Example 3, the subject matter of Example 2 is optionally configured such that the protrusions are sized to provide point contact with the bone to maintain the instrument body in the first position In Example 4, the subject matter of any one of Examples 1-3 is optionally configured such that the guide is configured to guide pin placement within the bone.

In Example 5, the subject matter of Example 4 is optionally configured such that the guide includes a hole including a longitudinal axis, wherein, with the instrument body in the first position, the longitudinal axis aligns with an axis of a guide pin.

In Example 6, the subject matter of any one of Examples 1-5 is optionally configured such that the guide is configured to guide a cutting device during resection of the bone.

In Example 7, the subject matter of Example 6 is optionally configured such that the guide includes a slot sized to allow the cutting device to pass through the slot, wherein, with the instrument body in the first position, the slot aligns with a resection plane of the bone.

In Example 8, the subject matter of any one of Examples 1-7 is optionally configured such that the protrusion extends outwardly from an interior surface of the instrument body.

In Example 9, the subject matter of any one of Examples 1-8 is optionally configured such that the instrument body is configured to extend at least partially around a distal end of a femur of the patient.

In Example 10, the subject matter of Example 9 is optionally configured such that the instrument body includes a condylar portion including a condylar protrusion extending from the condylar portion and configured to be sized according to the anatomy of the bone to abut a condyle of the femur of the patient.

In Example 11, the subject matter of Example 10 is optionally configured such that the instrument body includes a patellar track portion including a patellar track protrusion extending from the patellar track portion and configured to be sized according to the anatomy of the bone to abut a patellar track of the femur of the patient.

Example 12 can include, or can optionally be combined with any one of Examples 1-11 to include subject matter that can include a bone resection system including an instrument body including a plurality of protrusions, each protrusion including an initial length and being configured to be sized to a final length according to an anatomy of a bone of a patient. The protrusions, in the respective final lengths, are configured to abut the patient's bone to provide point contact with the bone and maintain the instrument body in a first position with respect to the bone during at least part of a resection procedure of the bone. A guide is configured to guide at least one aspect of the resection procedure.

In Example 13, the subject matter of Example 12 is optionally configured such that the guide is configured to guide pin placement within the bone.

In Example 14, the subject matter of Example 13 is optionally configured such that the guide includes a hole including a longitudinal axis, wherein, with the instrument body in the first position, the longitudinal axis aligns with an axis of a guide pin.

In Example 15, the subject matter of any one of Examples 12-14 is optionally configured such that the guide is configured to guide a cutting device during resection of the bone.

In Example 16, the subject matter of Example 15 is optionally configured such that the guide includes a slot sized to allow the cutting device to pass through the slot, wherein, with the instrument body in the first position, the slot aligns with a resection plane of the bone.

In Example 17, the subject matter of any one of Examples 12-16 optionally includes a protrusion-sizing tool configured to size the protrusions to the respective final lengths.

In Example 18, the subject matter of Example 17 is optionally configured such that the protrusion-sizing tool includes a cutting portion configured to cut one or more of the protrusions to size each of the one or more protrusions to the respective final lengths.

In Example 19, the subject matter of any one of Examples 17-18 is optionally configured such that the protrusion-sizing tool includes a measurement portion configured to measure a length of one or more of the protrusions.

Example 20 can include, or can optionally be combined with any one of Examples 1-19 to include subject matter that can include an apparatus including an instrument body including a plurality of protrusions. Each protrusion includes an initial length and being configured to be sized to a final length according to an anatomy of a bone of a patient. The protrusions, in the respective final lengths, are configured to abut the patient's bone to provide point contact with the bone and maintain the instrument body in a first position with respect to the bone during at least part of the resection procedure. A guide includes a hole including a longitudinal axis, wherein, with the instrument body in the first position, the longitudinal axis aligns with an axis of a guide pin to guide pin placement within the bone. A slot is sized to allow a cutting device to pass through the slot, wherein, with the instrument body in the first position, the slot aligns with a resection plane of the bone to guide a cutting device during resection of the bone.

DETAILED DESCRIPTION

The present patent application relates to apparatuses, systems, and methods related to a joint replacement procedure apparatus customized according to the specific anatomy of a patient and use thereof during a joint replacement procedure. Customized joint replacement instruments can be relatively expensive and can require increased lead time to prepare compared to standard joint replacement instruments. The present patent application describes customization of a joint replacement procedure apparatus in a timely and cost-efficient manner, so as to obtain benefits of using customized instruments with a decreased expense and lead time compared to those of customized joint replacement instruments.

Although herein described mostly with respect to knee replacement procedures, the present subject matter is not so limited and, in some examples, can be used with respect to other joint replacement procedures, such as, but not limited to hip replacement procedures and shoulder replacement procedures.

Referring to FIGS. 1-6, in some examples, an apparatus 100 can include a joint replacement procedure apparatus 100. In some examples, the joint replacement procedure apparatus 100 includes an instrument body 110. In some examples, the instrument body 110 is sized and shaped to correspond to a bone 10 of the patient. In further examples, the instrument body 110 is sized and shaped to correspond to a human femur 10. In still further examples, the instrument body 110 is sized and shaped to correspond to a distal end 12 of the human femur 10. In other examples, the instrument body can be sized and shaped to correspond to other bones, human or animal, or other parts of an anatomy, human or animal.

Figure 1:
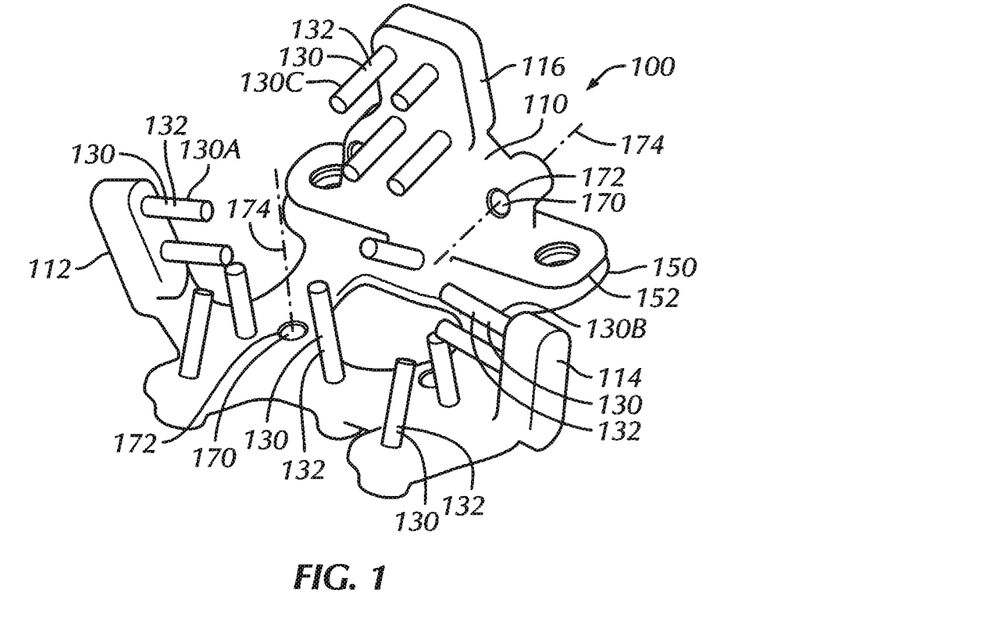
FIG. 1 is a perspective view of a customizable joint replacement procedure apparatus in accordance with at least one example of the invention.
Figure 2:
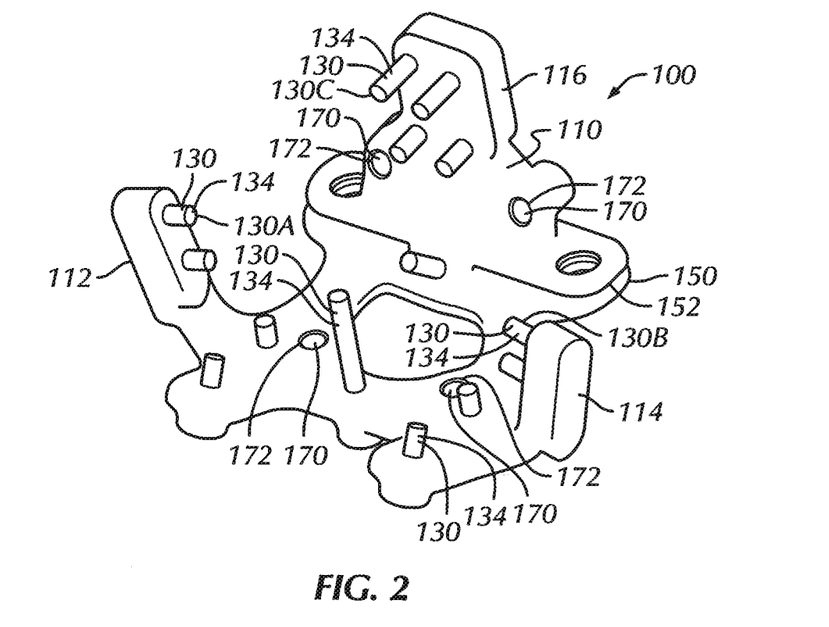
FIG. 2 is a perspective view of a customizable joint replacement procedure apparatus in accordance with at least one example of the invention, wherein protrusions of the customizable joint replacement procedure apparatus have been sized to customize the customizable joint replacement procedure apparatus to fit a patient's bone.

In some examples, the instrument body 110 includes a protrusion 130 configured to be sized according to an anatomy of a patient. In some examples, the protrusion 130 is configured to be sized according to an anatomy of a bone 10 of the patient. In some examples, the protrusion 130 includes an initial length 132, and, based upon measurements taken of the anatomy of the patient, the protrusion 130 can be sized to a final length 134 for placement of the apparatus 100 with respect to the bone 10 of the patient.

In some examples, an image or a series of images of the patient can be taken using one or more of various imaging techniques, including, but not limited to, radiography, computed tomography, magnetic resonance imaging (MRI), or sonography. For instance, the particular portion of the anatomy of the patient, such as, but not limited to a joint, can be imaged using an imaging technique. Using an image or series of images, in some examples, a physician or other user can virtually position a likeness of the instrument body 110 with respect to the anatomy of the patient (for instance, using software or an algorithm). With the likeness of the instrument body 110 positioned with respect to the image or series of images of the anatomy of the patient, a virtual measurement of the protrusion 130 can be made (for instance, using software or an algorithm) to determine a final length 134 of the protrusion 130 to which to size the protrusion 130 in order to obtain the desired position of the instrument body 110 with respect to the anatomy of the patient during the procedure. In this way, the protrusion 130 can then be cut to the final length 134 to substantially customize the instrument body 110 for the anatomy of the patient in order to use the apparatus 100 for the procedure.

In some examples, the instrument body 110 includes more than one protrusion 130. In some examples, the protrusions 130 are sized to provide point contact with the bone 10 to maintain the instrument body 110 in the first position. In some examples, the one or more protrusions 130, in the respective final lengths 134, are configured to abut the patient's bone 10 to provide point contact with the bone 10 and maintain the instrument body 110 in the first position with respect to the bone 10 during at least part of the resection procedure. In some examples, in the first position, the instrument body 110 is positioned on the bone 10 to facilitate a resection of the bone 10 along a distal resection plane 14 (see FIG. 8). In some examples, the number of protrusions 130 is sufficient to allow positioning of the apparatus 100 on the bone 10 in the desired position with little to no wobbling or other movement with respect to the bone 10. In some examples, the instrument body 110 includes at least three protrusions 130 in order to establish sufficiently stable contact with the bone 10. In some examples, the instrument body 110 includes more than three protrusions 130. In some examples, the one or more protrusions extend outwardly from an interior surface of the instrument body 110. In some examples, the instrument body 110 is configured to extend at least partially around a portion of the bone 10 of the patient. In further examples, the instrument body 110 is configured to extend at least partially around the distal end 12 of the bone 10. In some examples, the instrument body 110 is configured to at least partially surround the portion of the bone 10, such that the interior surface substantially faces the portion of the bone 10.

In some examples, the instrument body 110 includes a first condylar portion 112 including at least one first condylar protrusion 130A extending from the first condylar portion 112 and configured to be sized according to the anatomy of the bone 10 to abut a first condyle 12A of the femur 10 of the patient. In some examples, the first condylar portion 112 includes more than one first condylar protrusion 130A extending from the first condylar portion 112. In some examples, the instrument body 110 includes a second condylar portion 114 including at least one second condylar protrusion 130B extending from the second condylar portion 114 and configured to be sized according to the anatomy of the bone 10 to abut a second condyle 12B of the femur 10 of the patient. In some examples, the second condylar portion 114 includes more than one second condylar protrusion 130B extending from the second condylar portion 114. In some examples, the instrument body 110 includes a patellar track portion 116 including a patellar track protrusion 130C extending from the patellar track portion 116 and configured to be sized according to the anatomy of the bone 10 to abut a patellar track 12C of the femur 10 of the patient. In some examples, the patellar track portion 116 includes more than one patellar track protrusion 130C extending from the patellar track portion 116. In some examples, the first condylar portion 112 substantially opposes the second condylar portion 114. In some examples, the one or more first condylar protrusions 130A and the one or more second condylar protrusions 130B extend substantially toward one another. In some examples, the patellar track portion 116 is disposed substantially intermediate the first condylar portion 112 and the second condylar portion 114. In some examples, the one or more patellar track protrusions 130C extend in a direction substantially perpendicular to a direction in which the one or more first condylar protrusions 130A or the second condylar protrusions 130B extend.

In some examples, the instrument body 110 includes a guide configured to guide an aspect of a resection procedure of the bone 10. In some examples, the protrusion 130, when sized to the final length 134, is configured to abut the patient's bone 10 to maintain the instrument body 110 in a first position with respect to the bone 10 during at least the aspect of the resection procedure.

In some examples, the guide includes a guide pin guide 170 configured to guide pin placement within the bone. In some examples, the guide pin guide 170 includes an opening or hole 172 in the instrument body 110. In some examples, the hole 172 includes a longitudinal axis 174 (FIG. 1), wherein, with the instrument body 110 in the first position, the longitudinal axis 174 aligns with an axis 184 of a guide pin 180 (see FIG. 6) disposed in the desired position with respect to the bone 10. In some examples, the guide pin guide 170 includes more than one hole 172, for instance, in order to guide placement of more than one guide pin 180. In some examples, such as that which is shown in FIG. 1, the guide pin guide 170 includes four holes 172, to allow for placement of up to four guide pins 180. In some examples, the four guide pins 180 can be positioned such that there are two distally-inserted guide pins 180 and two anteriorly-inserted guide pins 180 within the bone 10. In various examples, the instrument body 110 includes one or more guide holes 172, positioned in a configuration that is standard for a particular type of tool or instrument or a product of a particular manufacturer, such that the apparatus 100 can be used to implant guide pins 180 to allow usage of the particular tool or instrument.

In some examples, the one or more guide holes 172 of the guide pin guide 170 can be used to align and guide a drill or other tool to make one or more holes in the bone 10 at one or more locations at which one or more guide pins 180 are to be placed. That is, once the apparatus 100 is in place with respect to the bone 10, a drill or other tool can be used with the apparatus 100, for instance, placing a drill bit or other tool within each of the one or more guide holes 172 of the guide pin guide 170 to drill a hole within the bone 10 at the one or more locations at which guide pins 180 are desired. Once the one or more holes are drilled or otherwise formed in the bone 10, one or more guide pins 180 can be placed through the one or more guide holes 172 of the guide pin guide 170 and secured to the bone 10 within the one or more holes drilled or otherwise formed in the bone 10. With the one or more guide pins 180 secured to the bone 10, the apparatus 100 is now secured to the bone 10 in the desired position and orientation (see FIG. 6). In other examples, prior to attaching the one or more guide pins 180 to the bone 10, but with the one or more holes drilled or otherwise formed in the bone 10, the apparatus 100 can be removed from the bone 10 and replaced with another apparatus or instrument configured for use with the procedure. For instance, referring briefly to FIG. 7, a cut guide apparatus 190 can be positioned with respect to the bone 10 and the one or more guide pins 180 can then be secured to the bone 10 using the one or more previously drilled or otherwise formed holes in the bone 10.

Referring again to FIGS. 1-6, in some examples, the guide includes a cut guide 150 configured to guide a cutting device (for instance, a bone saw or the like) during resection of the bone 10. In some examples, the cut guide 150 includes a slot 152 sized to allow the cutting device to pass through the slot 152, wherein, with the instrument body 110 in the first position, the slot 152 aligns with the resection plane 14 (see FIG. 8) of the bone 10. In this way, with the apparatus 100 secured to the bone 10 (for instance, using one or more guide pins 180, as described herein), a bone saw or other tool can be disposed within the slot 152 to guide cutting of the bone 10 along the resection plane 14. In the example shown in FIGS. 5 and 6, the resection plane 14 aligns with a distal resection 20 (see FIG. 8) of the bone 10. In other examples, the slot 152 of the cut guide 150 can align with other resections of the bone, in addition to or instead of the distal resection, such as one or more of an anterior resection 22, a posterior resection 24, chamfer resections 26, 28, or the like (see FIG. 8).

Figure 10:
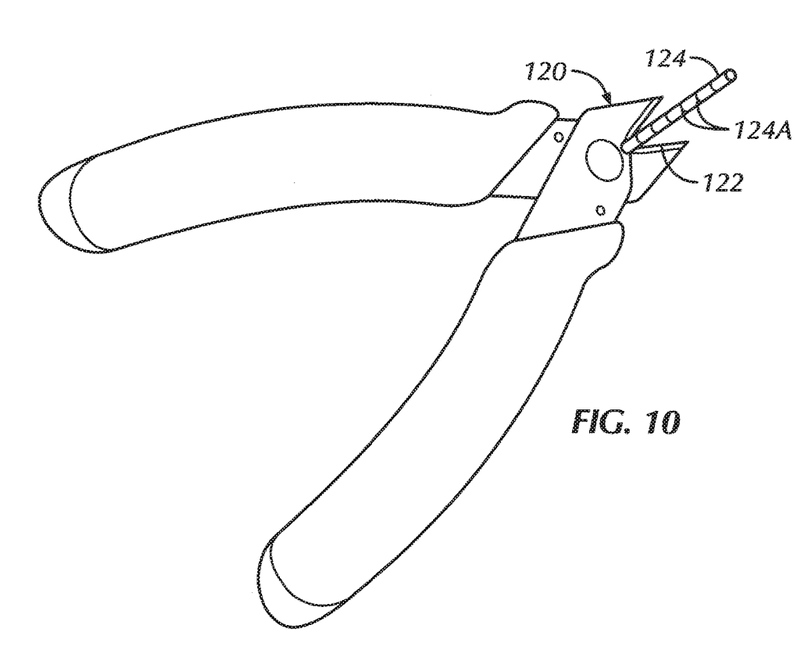
FIG. 10 is a protrusion-sizing tool in accordance with at least one example of the invention.

Referring to FIG. 10, in some examples, a bone resection system can include the apparatus 100, as described herein. In some examples, the bone resection system can include a protrusion-sizing tool 120 configured to size the one or more protrusions 130 to the respective final lengths 134. In some examples, the one or more protrusions 130 can be integrally formed with or otherwise affixed to the instrument body 110. In some examples, if the desired final length of the one or more protrusions 130 is shorter than the initial length 132, the one or more protrusions 130 can be cut to the final length 134 using the protrusion-sizing tool 120. In some examples, the protrusion-sizing tool 120 includes a cutting portion 122 configured to cut one or more of the one or more protrusions 130 to size each of the one or more protrusions 130 to the respective final lengths 134. In some examples, the cutting portion 122 includes at least one blade or sharpened surface. In some examples, the cutting portion 122 includes one blade or sharpened portion actuatable toward or against a surface, such that, with the protrusion 130 disposed between the blade or sharpened portion and the surface, actuation of the blade or sharpened portion toward or against the surface cuts, pinches, breaks, or otherwise removes a portion of the protrusion 130. Actuation of the blade or sharpened portion toward the surface, in some examples, can be accomplished with relative rotational movement or relative translational movement of the blade or sharpened portion with respect to the surface. In some examples, the cutting portion 122 includes two blades or sharpened portions actuatable toward or against one another, such that, with the protrusion 130 disposed between the blades or sharpened portions, actuation of the blades or sharpened portions toward or against one another cuts, pinches, breaks, or otherwise removes a portion of the protrusion 130. Actuation of the blades or sharpened portions toward or against one another, in some examples, can be accomplished with relative rotational movement or relative translational movement of the blades or sharpened portions with respect to each other.

In some examples, the protrusion-sizing tool 120 includes a measurement portion 124 configured to measure a length of one or more of the protrusions 130. In some examples, the measurement portion 124 includes a scale 124A or other markings to denote various lengths, such that, with the measurement portion 124 disposed at or otherwise proximate the protrusion 130, the physician or other user can determine, using the scale 124A or other markings of the measurement portion 124, the position of the cutting portion 122 with respect to the protrusion 130, such that, after cutting of or otherwise sizing the protrusion 130, the final length 134 of the protrusion 130 corresponds to the position on the scale 124A or other markings at which the cutting portion 122 was placed. In some examples, the measurement portion 124 is adjustable with respect to the cutting portion 122, such that the one or more protrusions 130 can be cut or otherwise sized to different lengths. That is, in some examples, the measurement portion 124 can be adjusted so that the cutting portion 122 cuts or otherwise sizes the protrusion 130 at the desired final length. In some examples, the measuring portion 124 is slidable with respect to the cutting portion 122. In some examples, the measuring portion 124 is threadably movable with respect to the cutting portion 122. In other examples, the protrusion-sizing tool 120 need not include the measuring portion 124. For instance, the one or more protrusions 130 can be measured and marked ahead of time, such that the protrusion-sizing tool 120 need only be used to cut the one or more protrusions at the markings made on the one or more protrusions 130.

In other examples, the one or more protrusions can include shafts movable with respect to the instrument body. For instance, in various examples, the one or more protrusions can include threaded shafts, slidable shafts, or the like. In some examples, one or more threaded protrusions can include a receptacle to accept a tool head in order to size the one or more protrusions. In such examples, the protrusion-sizing tool can include a tool similar to a hex wrench, a screwdriver, or the like. In other examples, the one or more threaded protrusions can be adjusted by turning the protrusions with fingers of the physician or other user. In some examples, one or more slidable protrusions are slidable using a protrusion-sizing tool, such as a hammer, pliers, or the like, for instance. In other examples, the one or more slidable protrusions can be adjusted by sliding or otherwise moving the protrusions with fingers of the physician or other user.

Figure 3:
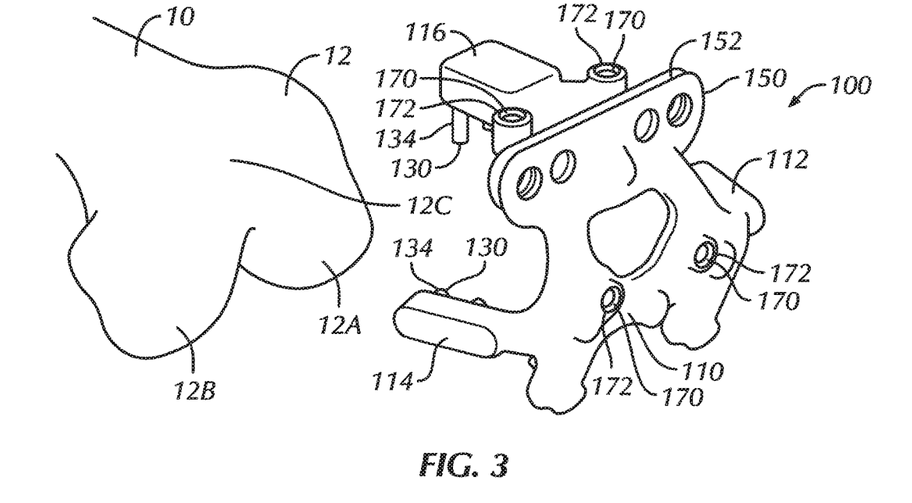
FIG. 3 is a perspective view of a customizable joint replacement procedure apparatus in accordance with at least one example of the invention, wherein the customizable joint replacement procedure apparatus is ready to be placed on a bone.
Figure 4:
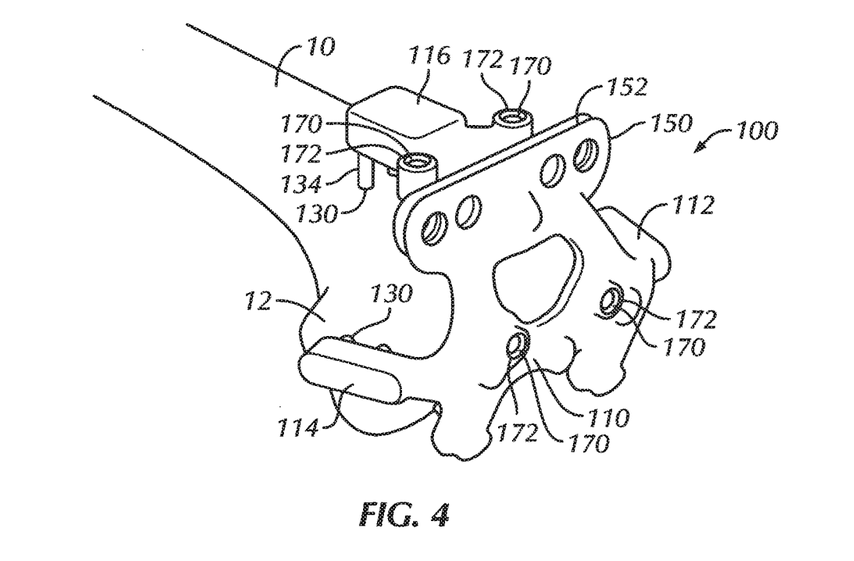
FIG. 4 is a perspective view of a customizable joint replacement procedure apparatus in accordance with at least one example of the invention, wherein the customizable joint replacement procedure apparatus is placed on a bone.
Figure 5:
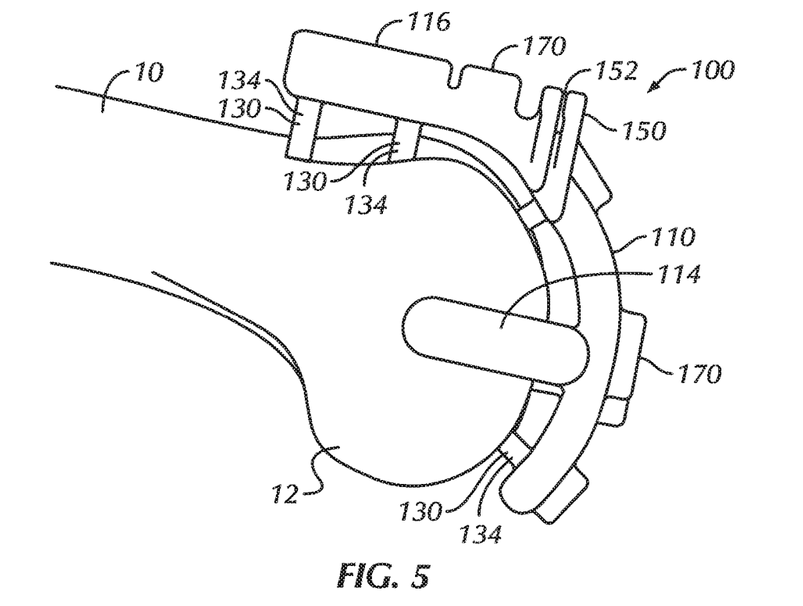
FIG. 5 is a side perspective view of a customizable joint replacement procedure apparatus in accordance with at least one example of the invention, wherein the customizable joint replacement procedure apparatus is placed on a bone.
Figure 6:
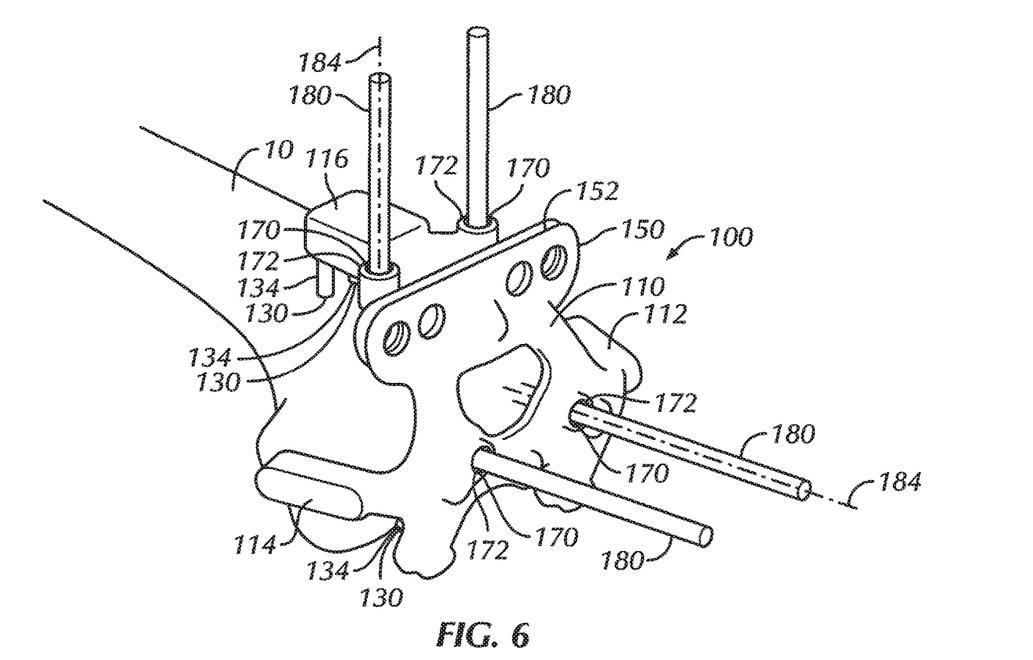
FIG. 6 is a perspective view of a customizable joint replacement procedure apparatus in accordance with at least one example of the invention, wherein the customizable joint replacement procedure apparatus is placed on a bone and secured with guide pins disposed within pin guides of the customizable joint replacement procedure apparatus.
Figure 7:
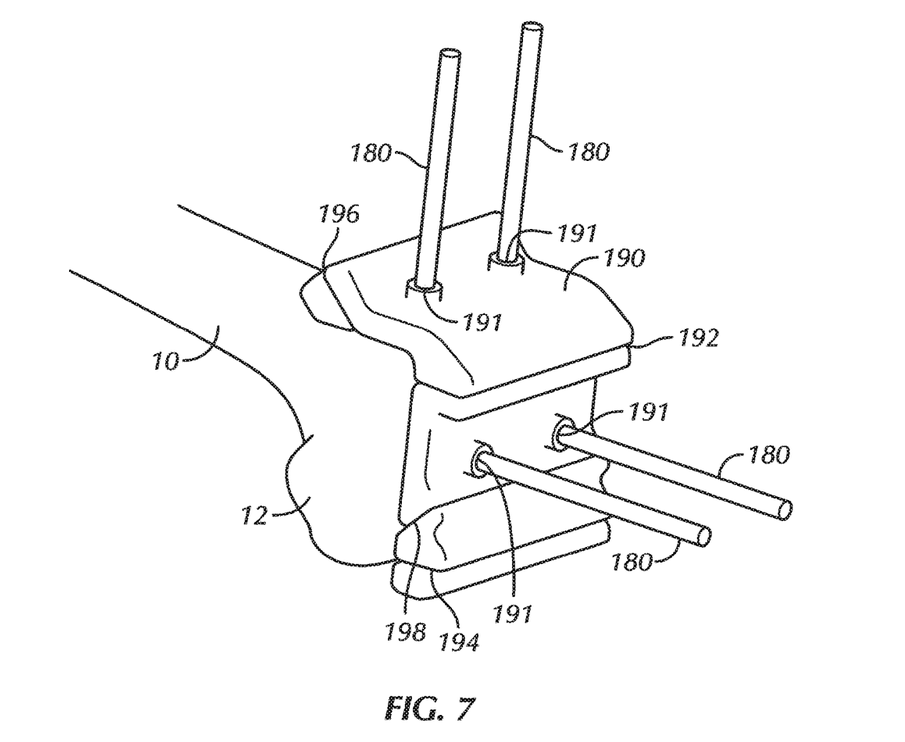
FIG. 7 is a perspective view of a cut guide apparatus in accordance with at least one example of the invention, wherein the cut guide apparatus is placed on a bone.
Figure 8:
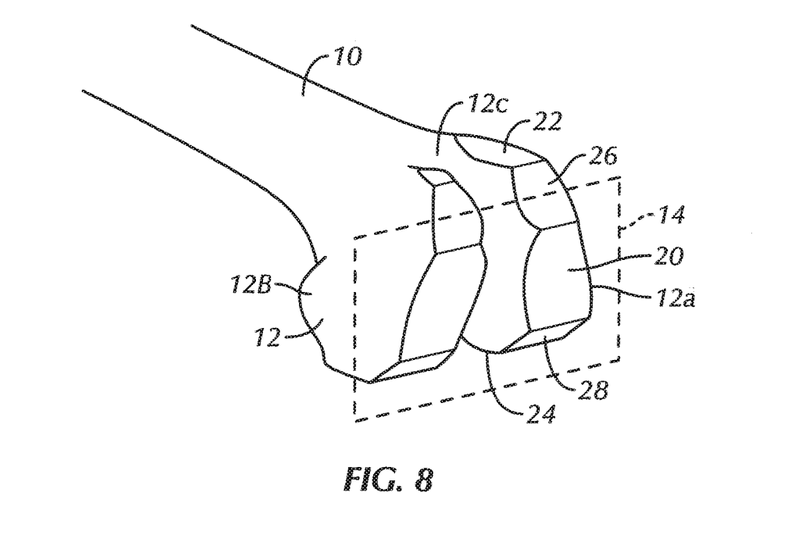
FIG. 8 is a perspective view of a resected bone.
Figure 9:
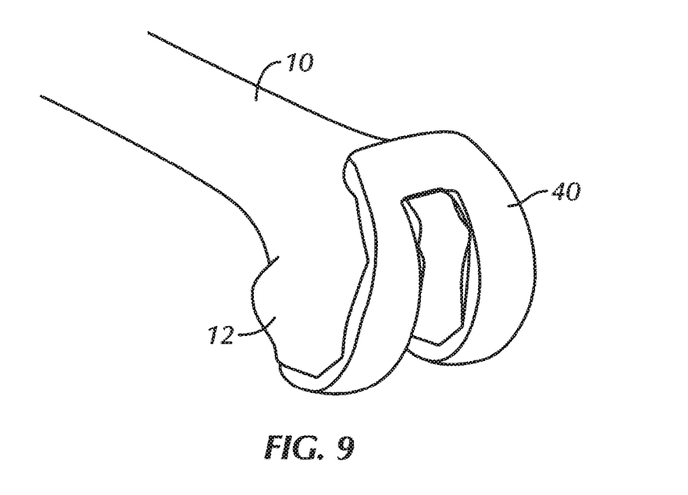
FIG. 9 is a perspective view of a bone including a prosthesis mounted on the bone.

Referring now to FIGS. 1-10, in use, in some examples, the physician or other user performs virtual measurements using images, as described herein, and, using the desired final length measurements for the protrusions 130, sizes the protrusions 130 of the instrument body 110 from the initial lengths 132 (FIG. 1) to the final lengths 134 (FIG. 2). The sizing of the protrusions 130, in some examples, is accomplished using the cutting portion 122 of the protrusion-sizing tool 120, as shown in FIG. 10. In further examples, the measuring and sizing of the protrusions 130 is accomplished using the measuring portion 124 and the cutting portion 122, respectively, of the protrusion-sizing tool 120. In other examples, the protrusions can be sized using a different protrusion-sizing tool or by hand. With the protrusions 130 sized to the respective final lengths 134, the instrument body 110 can be positioned with respect to the bone 10, as shown in FIGS. 3-5. In further examples, the instrument body 110 is placed in abutting contact with the distal end 12 of the bone 10. In still further examples, the instrument body 110 is placed in abutting contact with the distal end 12 of the femur 10. With the instrument body 110 in position with respect to the bone 10, holes can be formed in the bone 10 using the guide holes 172 of the guide pin guide 170, and the guide pins 180 can be affixed to the bone 10, as shown in FIG. 6. The distal end 12 of the bone 10, in some examples, is then cut with a bone saw or other device, tool, or instrument using the slot 152 of the cut guide 150 to guide the bone saw or other device, tool, or instrument. In some examples, cutting the bone 10 using the cut guide 150 enables a distal resection 20 of the bone 10, as shown in FIG. 8. In some examples, either in addition to or instead of the distal resection 20, the cut guide 150 can be configured to allow one or more other resections, such as, but not limited to, the anterior resection 22, the posterior resection 24, the anterior chamfer resection 26, or the posterior chamfer resection 28, as shown in FIG. 8. In some examples, once at least the guide pins 180 are located within the bone 10, the instrument body 110 can be removed and the cut guide apparatus 190 can be positioned on the bone 10. In some examples, the cut guide apparatus 190 is configured to be attached to the bone 10 having the distal resection 20. In some examples, referring to FIGS. 7 and 8, the cut guide apparatus 190 allows for one or more of the following resections of the bone 10: the anterior resection 22 using an anterior slot 192, the posterior resection 24 using a posterior slot 194, the anterior chamfer resection 26 using an anterior chamfer slot 196, or the posterior chamfer resection 28 using a posterior chamfer slot 198. Once all the resections of the bone are performed, in some examples, the guide pins 180 and, if used, the cut guide apparatus 190 are removed from the bone 10, as shown in FIG. 8. Referring to FIG. 9, in some examples, the resections of the bone 10 allow for mating and attachment of a prosthesis 40, for instance, for use in a joint replacement. In some examples, the prosthesis 40 includes a bearing surface for attachment to the distal end 12 of the femur 10 for use in a knee replacement. In other examples, the prosthesis can include other implanted components or devices for use in other procedures, including, but not limited to other joint replacement procedures, such as shoulder replacement procedures or hip replacement procedures.

The present inventors have recognized various advantages of the subject matter described herein. For instance, in some examples, the present subject matter allows for a customized tool or instrument to be used for a particular patient without having to wait for the customized tool or instrument to be specially manufactured and shipped to the physician or other user. That is, the physician or other user can customize a standard tool or instrument before or during the procedure, decreasing costs and lead time needed before the procedure from the costs and lead time needed for a specially-made tool or instrument. While various advantages of the example apparatuses, systems, and methods are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description. The drawings show, by way of illustration, specific examples in which the present apparatuses and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the minis "including" and "comprising" are open-ended, that is, an apparatus or method that includes elements in addition to those listed after such a tent' in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. A joint replacement procedure apparatus for use in a knee replacement procedure, the apparatus comprising:
   an instrument body configured to have a first, standard configuration and a second, customized configuration, the instrument body including:
      a plurality of protrusions, each protrusion including an initial length with the instrument body in the first, standard configuration, each protrusion being configured to be sized to a final length according to an anatomy of a bone of a patient to place the instrument body in the second, customized configuration, the protrusion being sized to the final length by removal of a portion of the protrusion from the protrusion; and
      a guide configured to guide an aspect of a resection procedure of the bone, wherein the protrusions, when sized to their respective final lengths with the instrument body in the second, customized configuration, are configured to abut the patient's bone to maintain the instrument body in a first position with respect to the bone during at least the aspect of the resection procedure.

2. The apparatus of claim 1, wherein the protrusions are sized to provide point contact with the bone to maintain the instrument body in the first position.

3. The apparatus of claim 1, wherein the guide is configured to guide pin placement within the bone.

4. The apparatus of claim 3, wherein the guide includes a hole including a longitudinal axis, wherein, with the instrument body in the first position, the longitudinal axis aligns with an axis of a guide pin.

5. The apparatus of claim 1, wherein the guide is configured to guide a cutting device during resection of the bone.

6. The apparatus of claim 5, wherein the guide includes a slot sized to allow the cutting device to pass through the slot, wherein, with the instrument body in the first position, the slot aligns with a resection plane of the bone.

7. The apparatus of claim 1, wherein the plurality of protrusions extend outwardly from an interior surface of the instrument body.

8. The apparatus of claim 1, wherein the instrument body is configured to extend at least partially around a distal end of a femur of the patient.

9. The apparatus of claim 8, wherein the instrument body includes a condylar portion including a condylar protrusion extending from the condylar portion and configured to be sized according to the anatomy of the bone to abut a condyle of the femur of the patient.

10. The apparatus of claim 9, wherein the instrument body includes a patellar track portion including a patellar track protrusion extending from the patellar track portion and configured to be sized according to the anatomy of the bone to abut a patellar track of the femur of the patient.

11. The apparatus of claim 1 in combination with a protrusion-sizing tool configured to remove a portion of one or more of the protrusions from the one or more protrusions to size the one or more protrusions to the respective final lengths.

12. A bone resection system for use in a knee replacement procedure, the system comprising:
an instrument body configured to have a first, standard configuration and a second, customized configuration, the instrument body including:
a plurality of protrusions, each protrusion including an initial length with the instrument body in the first, standard configuration, each protrusion being configured to be cut to a final length according to an anatomy of a bone of a patient to place the instrument body in the second, customized configuration, the protrusions, in the respective final lengths with the instrument body in the second, customized configuration, being configured to abut the patient's bone to provide point contact with the bone and maintain the instrument body in a first position with respect to the bone during at least part of a resection procedure of the bone; and
a guide configured to guide at least one aspect of the resection procedure, and
a protrusion-sizing tool configured to cut one or more of the protrusions to the respective final lengths to place the instrument body in the second, customized configuration.

13. The bone resection system of claim 12, wherein the guide is configured to guide pin placement within the bone.

14. The bone resection system of claim 13, wherein the guide includes a hole including a longitudinal axis, wherein, with the instrument body in the first position, the longitudinal axis aligns with an axis of a guide pin.

15. The bone resection system of claim 12, wherein the guide is configured to guide a cutting device during resection of the bone.

16. The bone resection system of claim 15, wherein the guide includes a slot sized to allow the cutting device to pass through the slot, wherein, with the instrument body in the first position, the slot aligns with a resection plane of the bone.

17. The bone resection system of claim 12, wherein the protrusion-sizing tool includes a cutting portion configured to cut the one or more of the protrusions to size each of the one or more protrusions to the respective final lengths.

18. The bone resection system of claim 12, wherein the protrusion-sizing tool includes a measurement portion configured to measure a length of one or more of the protrusions.

19. A joint replacement procedure apparatus for use in a knee replacement procedure, the apparatus comprising:
an instrument body configured to have a first, standard configuration and a second, customized configuration, the instrument body including:
a plurality of protrusions, each protrusion including an initial length with the instrument body in the first, standard configuration, each protrusion being configured to be cut to a final length according to an anatomy of a bone of a patient to place the instrument body in the second, customized configuration, the protrusions, in the respective final lengths with the instrument body in the second, customized configuration, being configured to abut the patient's bone to provide point contact with the bone and maintain the instrument body in a first position with respect to the bone during at least part of the resection procedure; and
a guide including:
a hole including a longitudinal axis, wherein, with the instrument body in the first position, the longitudinal axis aligns with an axis of a guide pin to guide placement of the guide pin within the bone; and
a slot sized to allow a cutting device to pass through the slot, wherein, with the instrument body in the first position, the slot aligns with a resection plane of the bone to guide a cutting device during resection of the bone.

20. The apparatus of claim 19 in combination with a protrusion-sizing tool configured to cut the protrusions to the respective final lengths.

* * * * *